(12) United States Patent
Rodriquez et al.

(10) Patent No.: US 6,832,572 B2
(45) Date of Patent: Dec. 21, 2004

(54) UNDERWATER DEPOSIT-RECOVERY SCOOPER AND SPECIMEN STORAGE CONTAINER

(75) Inventors: Robert A. Rodriquez, Raynham, MA (US); Michael Nicholson, Picayne, MS (US)

(73) Assignee: Academy of Applied Science

( * ) Notice: Subject to any disclaimer, the term of this patent is extended or adjusted under 35 U.S.C. 154(b) by 0 days.

(21) Appl. No.: 10/448,523

(22) Filed: Apr. 25, 2003

(65) Prior Publication Data

US 2004/0211349 A1 Oct. 28, 2004

(51) Int. Cl.$^7$ ................................................ B63G 8/00
(52) U.S. Cl. ..................... 114/312; 37/341; 114/313; 114/321
(58) Field of Search ................................. 114/312, 313, 114/321; 37/307, 313, 341

(56) References Cited

U.S. PATENT DOCUMENTS

| | | | | |
|---|---|---|---|---|
| 3,626,703 A | * | 12/1971 | Richburg | 405/191 |
| 3,892,079 A | * | 7/1975 | Hirano et al. | 37/309 |
| 3,929,533 A | * | 12/1975 | Horn | 156/71 |
| 4,574,502 A | * | 3/1986 | Blau | 37/266 |

FOREIGN PATENT DOCUMENTS

| | | | |
|---|---|---|---|
| GB | 1311848 | * | 3/1973 |
| GB | 1583862 | * | 2/1981 |

* cited by examiner

*Primary Examiner*—Sherman Basinger
(74) *Attorney, Agent, or Firm*—Rines and Rines

(57) ABSTRACT

A transparent/translucent flexible resilient plastic scooper container for operation by underwater remotely operated vehicle jaws, having a flat-bottomed lower portion hollow bowl and an upper inverted bowl lid rearwardly hinged thereto and resiliently insertable into and withdrawable from the hollow of the lower portion by the closing and opening of the jaws.

12 Claims, 2 Drawing Sheets

Figure 1:
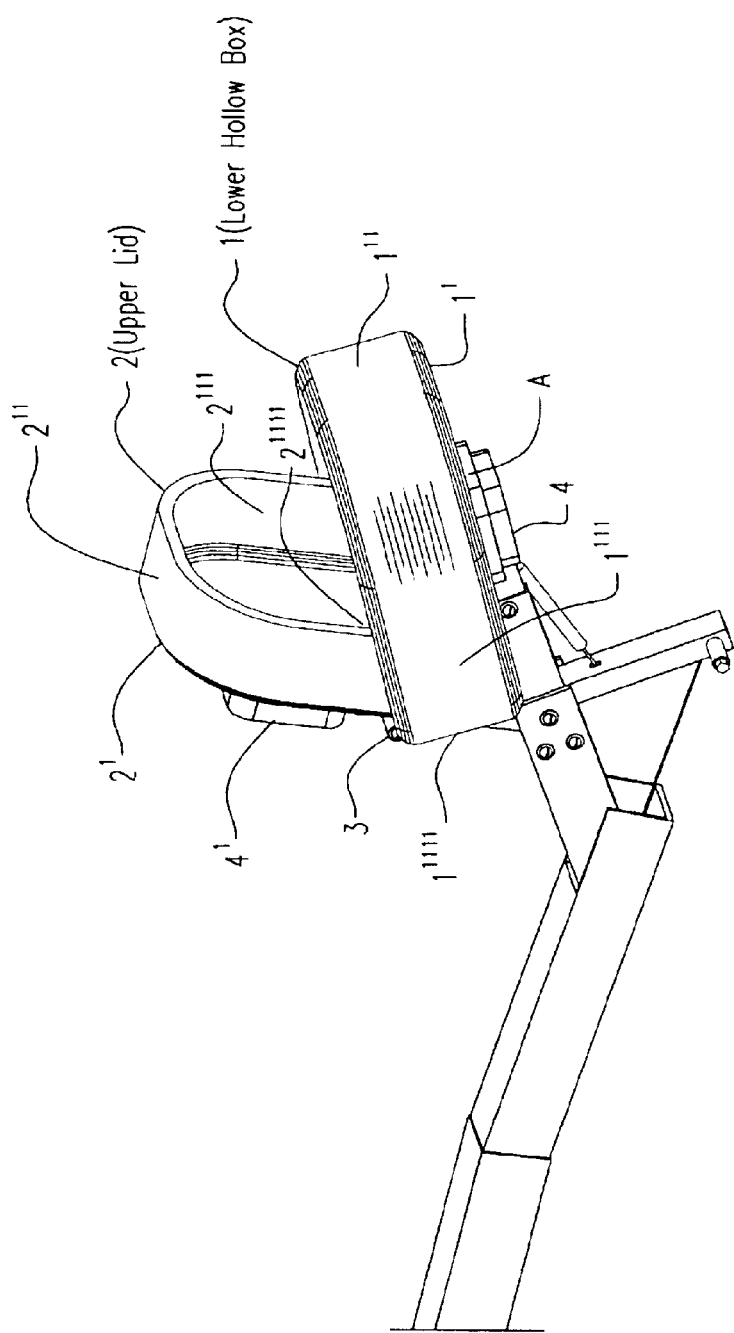

(Jaws and assembly not shown for clarity.)

UNDERWATER DEPOSIT-RECOVERY SCOOPER AND SPECIMEN STORAGE CONTAINER

FIELD

The invention relates to the recovery of underwater deposits of all sorts by underwater vehicles and the like, including those equipped with mechanical arm-jaw-operated containers; being more particularly concerned with "clam-shell" type scoopers that can seal the scooped deposit during its raising to the surface of the water.

BACKGROUND

Many types of underwater deposit recovery mechanisms, containers, corers and the like have been proposed and used, particularly in connection with remote-controlled underwater vehicles (ROV), monitored by underwater television and other cameras. An example of such is described for example in "Discovering the Oceans", published by the University National Oceanographic Laboratory System in December 2000, and elsewhere.

Such devices are relatively expensive and are not particularly adapted for smaller ROV mechanical recovery arms and jaws. They generally require, moreover, special sealing mechanisms and dimensional fit tolerances, and, in addition, often require the removal of recovered deposits and transfer to storage containers, sampler bottles and the like.

In accordance with the present invention an improved, simplified and low-cost recovery "clam-shell" type scooper is provided that is preferably made of one-piece resilient transparent or translucent thin plastic for observation of contents and that self-seals and can itself, indeed, serve as the ultimate specimen storage container, being readily detachable from the operational jaws for such purpose.

OBJECTS OF INVENTION

The principal object of the present invention, thus, is to provide such a simplified and low-cost underwater and self-sealing scooper, particularly adapted to be connected to (detachably, if desired) mechanical arm jaws carried by underwater vehicles such as ROV's and the like, and that may also be used as the ultimate storage container for the recovered deposits, and that shall not be subject to the above-described and other limitations of present-day devices of this nature.

Other and further objects % will be explained hereinafter and are more specifically delineated by the appended claims.

SUMMARY

In summary, the invention embraces a transparent/translucent thin flexible plastic scooper-container having lower and upper mating hollow container portions having rearward and forward walls and side walls therebetween and joined along their adjacent rearward walls by an intermediate flexible resilient hinge region, and with the upper portion inverted and normally resiliently hold diverging upward at an acute or obtuse angle from the lower portion in an open scooper-container position; the upper portion being of somewhat smaller cross dimensions and area than the lower position to permit a forced resilient downwardly bending insertion of the upper portion into the lower portion about said hinge region to fit into the hollow of the lower portion and with its forward wall engaging the bottom of the lower portion rearward of its forward wall, thereby to close off the hollows between the upper and lower portions in a closed scooper-container position.

Best mode and preferred designs are later described in detail.

DRAWINGS

The invention will now be described in connection with the accompanying drawing, FIGS. 1 and 2 of which are isometric views of a preferred embodiment respectively in open scooper position and in closed, self-sealed position.

Preferred Embodiment(s)

Figure 2:
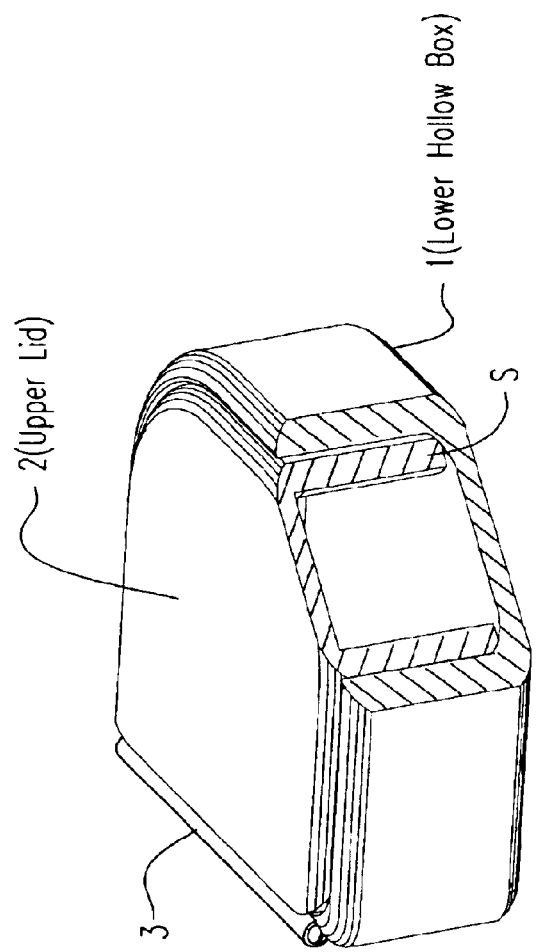

Referring to FIG. 1, a thin transparent/translucent plastic scooper box-like container as of resilient sheet polyethylene plastic or the like, is shown having a generally rectangular lower portion hollow box or bowl-like shape at 1, defined by a flat bottom $1^1$ bounded by forward, side and rearward walls $1^{11}$, $1^{111}$ and $1^{1111}$, respectively. Hingedly intermediately and resiliently connected at 3 along the top rear edge of the rearward wall $1^{1111}$, is an insertable somewhat smaller-area and dimensioned hollow inverted box or bowl-like upper portion lid 2 having a flat top surface $2^1$ bounded by respective forward side and rearward walls $2^{11}$, $2^{111}$ and $2^{1111}$, and normally resiliently held open at an acute or obtuse angle. The lid is resiliently insertable when bent downwardly about the rearward wall hinge region 3 into the hollow of the lower portion 1 and into the closed container position, of FIG. 2.

The ends of deploying jaws $4$-$4^1$ as of an underwater ROV, are shown attached at respective regions on the top of the lid $2^1$ and the outer bottom wall $1^1$ of the lower box portion 1 by any suitable fittings (including adhesive patches) which may be readily attached to or detached from the jaw ends shown at A. In response to the pivoted clamping of the jaws $4$-$4^1$ on the ROV (or other support), a forced resiliently downwardly bending insertion of the upper lid portion 2 into the hollow of the lower portion 1 about the hinge region 3 will occur, closing off the acute open angle, and with the forward edge of the forward wall of the lid engaging the inner lower portion of the forward wall $1^{11}$ along a closing seal region S, FIG. 2, held closed by the clamping force of the closed jaws.

If desired, the total structure 1-2-3 may be of a single molded shaped piece, with the hinge bending line 3 of thinner plastic for more easy jaw controlling by a small motor; or the hinge region 3 may be a resilient strip or other simple spring hinge joining the upper rearward wall edge $1^{111}$ of the lower portion to a separate upper portion inverted flap lid 2.

Once the scoop has recovered a deposit therein as observable by underwater video, the remote closing of the jaws will force-clamp the upper portion lid 2 inside the lower portion box 1 with a resilient pressure seal or tight fit S along the peripheral edges of the lid forward and side walls, somewhat like a calm shell. A fastener such as a latch or a seal by piece a tape (not shown) will hold the device closed if the container is then to be detached from the jaw fittings and released to be used as a storage container.

Further modifications will also occur to those skilled in this art and such are considered to fall within the spirit and scope of the invention as defined in the appended claims.

What is claimed is:

1. A transparent/translucent thin flexible plastic scooper-container having lower and upper mating hollow container portions having rearward and forward edges and side walls therebetween and joined along their adjacent rearward edges by a flexible intermediate resilient hinge region, and with the upper portion inverted and normally resiliently held diverging at an acute or obtuse angle from the lower portion in an open scooper-container position the upper portion being of somewhat smaller cross dimensions and area than the lower portion to permit a forced resilient downwardly bending insertion of the upper portion into the lower portion about said hinge region to fit into the hollow of the lower portion, and with its forward edge engaging the bottom of the lower portion rearward of its forward edge, thereby to close off the hollows between the upper and lower portions in a closed scooper-container position.

2. The scooper-container of claim 1 wherein the upper and lower portions and intermediate hinge region are formed as an integral single plastic piece, normally resiliently sprung in said open position.

3. The scooper-container of claim 2 wherein said hinge region is thinned to reduce the required resilient closing force needed to achieve the said closed position.

4. The scooper-container of claim 1 wherein said hinge region is thin compared to the plastic of the container to minimize the required resilient closing force needed to achieve said closed portion.

5. The scooper-container of claim 1 wherein the outer top surface of the upper portion and the outer bottom surface of the lower portion are each provided with attachment regions for attachment to the open ends of underwater-vehicle mechanical jaws for applying closing and opening forces.

6. The scooper-container of claim 5 wherein the vehicle is remotely operated underwater and provided with video camera monitoring, and with the scooping of deposits into the lower portion and the capturing of the same during closing being viewable during said monitoring through the translucent or transparent container walls, and thus controllable by remote operation of the jaws.

7. The scooper-container of claim 5 wherein the attachment regions are provided with means for enabling ready detachment from the ends of the jaws and, after fastening the closed scooper, provides a sealed removable container for the deposits captured by the scooper.

8. The scooper-container of claim 1 wherein the container portions simulate a "clam shell" structure.

9. The scooper-container of claim 8 wherein the lower portion is substantially a bowl with a flat bottom, and the upper position is substantially an inverted bowl flap lid for resilient insertion into and withdrawing from, the hollow of the lower portion.

10. The scooper-container of claim 1 wherein the fitting of the upper portion into the lower portion creates a tight fit or seal in said closed position.

11. A transparent/translucent flexible resilient plastic scooper container for operation by underwater remotely operated vehicle jaws, having a flat-bottomed lower portion hollow bowl and an upper inverted bowl lid rearwardly hinged thereto and resiliently insertable into and withdrawable from the hollow of the lower portion by the closing and opening of the jaws, and with the forward edge of the lid engaging the bottom of the lower bowl portion rearward of its forward edge when the lid is fully inserted into the lower portion.

12. A transparent/translucent flexible thin plastic scooper and container as for underwater deposits having, in combination, a lower box portion and an upper inverted box-like lid resiliently fittable therein and rearwardly attached thereto at an acute angle in a resiliently held open position; the lid being resiliently bendable downwardly in response to a clamping force to force the lid into the box portion and close off the angle; the lid thereupon sealing against the box portion during the continued application of such clamping and with the forward edge of the lid engaging the bottom of the box portion rearward of its forward edge.

* * * * *